(12) United States Patent
Reicher et al.

(10) Patent No.: US 9,836,202 B1
(45) Date of Patent: *Dec. 5, 2017

(54) SYSTEMS AND METHODS FOR VIEWING MEDICAL IMAGES

(71) Applicant: DR Systems, Inc., San Diego, CA (US)

(72) Inventors: Murray A. Reicher, Rancho Santa Fe, CA (US); Evan K. Fram, Paradise Valley, AZ (US)

(73) Assignee: D.R. SYSTEMS, INC., San Diego, CA (US)

( * ) Notice: Subject to any disclaimer, the term of this patent is extended or adjusted under 35 U.S.C. 154(b) by 384 days.

This patent is subject to a terminal disclaimer.

(21) Appl. No.: 14/540,830

(22) Filed: Nov. 13, 2014

Related U.S. Application Data

(63) Continuation of application No. 13/477,853, filed on May 22, 2012, now Pat. No. 8,913,808, which is a continuation of application No. 13/228,349, filed on Sep. 8, 2011, now Pat. No. 8,244,014, which is a continuation of application No. 12/702,976, filed on Feb. 9, 2010, now Pat. No. 8,019,138, which is a continuation of application No. 11/179,384, filed on Jul. 11, 2005, now Pat. No. 7,660,488.

(60) Provisional application No. 60/625,690, filed on Nov. 4, 2004.

(51) Int. Cl.
*G06F 15/00* (2006.01)
*G06F 3/0484* (2013.01)
*G06F 3/16* (2006.01)

(52) U.S. Cl.
CPC .......... *G06F 3/04845* (2013.01); *G06F 3/167* (2013.01)

(58) Field of Classification Search
CPC ................................ G06T 1/20; G06T 15/005
USPC ........................................................ 345/501
See application file for complete search history.

(56) References Cited

U.S. PATENT DOCUMENTS

| 5,172,419 A | 12/1992 | Manian |
| 5,515,375 A | 5/1996 | DeClerck |
| 5,807,256 A | 9/1998 | Taguchi |
| 5,835,030 A | 11/1998 | Tsutsui et al. |
| 5,857,030 A | 1/1999 | Gaborski |
| 6,008,813 A | 12/1999 | Lauer et al. |

(Continued)

OTHER PUBLICATIONS

U.S. Appl. No. 13/572,397, filed Aug. 10, 2012, Reicher.

(Continued)

*Primary Examiner* — Jin Ge
(74) *Attorney, Agent, or Firm* — Knobbe Martens Olson & Bear LLP

(57) ABSTRACT

For certain medical images, it is important and/or required that a user view all of a medical image at full resolution so that minute, but important, indicia in the medical image are not missed. A computing systems monitor the portions of the medical image that are displayed on the display device, notates those portions that have been displayed at full resolution (or other user-defined display parameters), and provides the user with information indicating portions that have not been viewed at full resolution and/or provides information indicating for which images of a multiple image examination full pixel display has been accomplished. The process reduces the possibility of missing an abnormality in a medical image due to the viewer not viewing a portion of the image at full resolution or using other user-defined display parameters.

20 Claims, 7 Drawing Sheets

(56) References Cited

U.S. PATENT DOCUMENTS

| | | | |
|---|---|---|---|
| 6,130,671 A | 10/2000 | Argiro | |
| 6,211,884 B1 | 4/2001 | Knittel et al. | |
| 6,219,059 B1 | 4/2001 | Argiro | |
| 6,219,061 B1 | 4/2001 | Lauer et al. | |
| 6,243,098 B1 | 6/2001 | Lauer et al. | |
| 6,262,740 B1 | 7/2001 | Lauer et al. | |
| 6,266,733 B1 | 7/2001 | Knittel et al. | |
| 6,297,799 B1 | 10/2001 | Knittel et al. | |
| 6,310,620 B1 | 10/2001 | Lauer et al. | |
| 6,313,841 B1 | 11/2001 | Ogata et al. | |
| 6,342,885 B1 | 1/2002 | Knittel et al. | |
| 6,356,265 B1 | 3/2002 | Knittel et al. | |
| 6,369,816 B1 | 4/2002 | Knittel et al. | |
| 6,404,429 B1 | 6/2002 | Knittel | |
| 6,407,737 B1 | 6/2002 | Zhao et al. | |
| 6,411,296 B1 | 6/2002 | Knittel et al. | |
| 6,421,057 B1 | 7/2002 | Lauer et al. | |
| 6,424,346 B1 | 7/2002 | Correll et al. | |
| 6,426,749 B1 | 7/2002 | Knittel et al. | |
| 6,427,022 B1 | 7/2002 | Craine et al. | |
| 6,476,810 B1 | 11/2002 | Simha et al. | |
| 6,512,517 B1 | 1/2003 | Knittel et al. | |
| 6,556,724 B1 | 4/2003 | Chang et al. | |
| 6,614,447 B1 | 9/2003 | Bhatia et al. | |
| 6,621,918 B1 | 9/2003 | Hu et al. | |
| 6,630,937 B2 * | 10/2003 | Kallergi | G01N 23/046 345/1.1 |
| 6,650,766 B1 | 11/2003 | Rogers | |
| 6,654,012 B1 | 11/2003 | Lauer et al. | |
| 6,680,735 B1 | 1/2004 | Seiler et al. | |
| 6,683,933 B2 | 1/2004 | Saito et al. | |
| 6,826,297 B2 | 11/2004 | Saito et al. | |
| 6,988,075 B1 | 1/2006 | Hacker | |
| 7,031,504 B1 | 4/2006 | Argiro et al. | |
| 7,039,723 B2 | 5/2006 | Hu et al. | |
| 7,136,064 B2 | 11/2006 | Zuiderveld | |
| 7,209,578 B2 | 4/2007 | Saito et al. | |
| 7,236,558 B2 | 6/2007 | Saito et al. | |
| 7,379,578 B2 | 5/2008 | Soussaline et al. | |
| 7,492,970 B2 | 2/2009 | Saito et al. | |
| 7,516,417 B2 | 4/2009 | Amador et al. | |
| 7,525,554 B2 | 4/2009 | Morita et al. | |
| 7,574,029 B2 | 8/2009 | Peterson et al. | |
| 7,590,272 B2 | 9/2009 | Brejl et al. | |
| 7,639,879 B2 | 12/2009 | Goto et al. | |
| 7,660,481 B2 | 2/2010 | Schaap et al. | |
| 7,835,560 B2 | 11/2010 | Vining et al. | |
| 7,885,828 B2 | 2/2011 | Glaser-Seidnitzer et al. | |
| 7,899,514 B1 | 3/2011 | Kirkland | |
| 7,970,188 B2 | 6/2011 | Mahesh et al. | |
| 7,991,210 B2 | 8/2011 | Peterson et al. | |
| 7,992,100 B2 | 8/2011 | Lundstrom et al. | |
| 8,073,225 B2 | 12/2011 | Hagen et al. | |
| 8,150,708 B2 | 4/2012 | Kotula et al. | |
| 8,214,756 B2 | 7/2012 | Salazar-Ferrer et al. | |
| 8,249,687 B2 | 8/2012 | Peterson et al. | |
| 8,262,572 B2 | 9/2012 | Chono | |
| 8,370,293 B2 | 2/2013 | Iwase et al. | |
| 8,797,350 B2 | 8/2014 | Fram | |
| 8,913,808 B2 | 12/2014 | Reicher et al. | |
| 9,042,617 B1 | 5/2015 | Reicher et al. | |
| 9,075,899 B1 | 7/2015 | Reicher | |
| 9,092,551 B1 | 7/2015 | Reicher | |
| 9,092,727 B1 | 7/2015 | Reicher | |
| 9,324,188 B1 | 4/2016 | Fram et al. | |
| 9,386,084 B1 | 7/2016 | Reicher et al. | |
| 9,471,210 B1 | 10/2016 | Fram et al. | |
| 9,495,604 B1 | 11/2016 | Fram | |
| 9,501,617 B1 | 11/2016 | Reicher et al. | |
| 9,501,627 B2 | 11/2016 | Reicher et al. | |
| 9,501,863 B1 | 11/2016 | Fram et al. | |
| 9,536,106 B2 | 1/2017 | Fram | |
| 9,536,324 B1 | 1/2017 | Fram | |
| 9,542,082 B1 | 1/2017 | Reicher et al. | |
| 9,672,477 B1 | 6/2017 | Reicher et al. | |
| 9,727,938 B1 | 8/2017 | Reicher et al. | |
| 2002/0070970 A1 * | 6/2002 | Wood | A61B 6/032 715/766 |
| 2002/0090119 A1 | 7/2002 | Saito et al. | |
| 2002/0110285 A1 | 8/2002 | Wang et al. | |
| 2002/0144697 A1 * | 10/2002 | Betz | A61B 6/00 340/573.1 |
| 2002/0172408 A1 | 11/2002 | Saito et al. | |
| 2002/0172409 A1 | 11/2002 | Saito et al. | |
| 2002/0186820 A1 | 12/2002 | Saito et al. | |
| 2002/0190984 A1 | 12/2002 | Seiler et al. | |
| 2003/0013951 A1 | 1/2003 | Stefanescu et al. | |
| 2003/0034973 A1 | 2/2003 | Zuiderveld | |
| 2003/0055896 A1 | 3/2003 | Hu et al. | |
| 2003/0101291 A1 | 5/2003 | Mussack et al. | |
| 2003/0130973 A1 | 7/2003 | Sumner, II et al. | |
| 2003/0156745 A1 | 8/2003 | Saito et al. | |
| 2003/0160095 A1 | 8/2003 | Segal | |
| 2004/0015703 A1 | 1/2004 | Madison et al. | |
| 2004/0105030 A1 | 6/2004 | Yamane | |
| 2004/0122705 A1 | 6/2004 | Sabol et al. | |
| 2005/0043970 A1 | 2/2005 | Hsieh | |
| 2005/0074150 A1 | 4/2005 | Bruss | |
| 2005/0107689 A1 | 5/2005 | Sasano | |
| 2005/0110791 A1 | 5/2005 | Krishnamoorthy et al. | |
| 2005/0143654 A1 | 6/2005 | Zuiderveld et al. | |
| 2005/0171818 A1 | 8/2005 | McLaughlin | |
| 2005/0251013 A1 | 11/2005 | Krishnan et al. | |
| 2005/0254729 A1 | 11/2005 | Saito et al. | |
| 2006/0061570 A1 * | 3/2006 | Cheryauka | G06T 11/006 345/424 |
| 2006/0122482 A1 | 6/2006 | Mariotti et al. | |
| 2006/0188134 A1 | 8/2006 | Quist | |
| 2006/0267976 A1 | 11/2006 | Saito et al. | |
| 2006/0276708 A1 | 12/2006 | Peterson et al. | |
| 2007/0009078 A1 | 1/2007 | Saito et al. | |
| 2007/0021977 A1 | 1/2007 | Elsholz | |
| 2007/0064984 A1 | 3/2007 | Vassa et al. | |
| 2007/0073556 A1 | 3/2007 | Lau et al. | |
| 2007/0106535 A1 | 5/2007 | Matsunaga | |
| 2007/0106633 A1 | 5/2007 | Reiner | |
| 2007/0109299 A1 | 5/2007 | Peterson | |
| 2007/0110294 A1 | 5/2007 | Schaap et al. | |
| 2007/0116345 A1 | 5/2007 | Peterson et al. | |
| 2007/0116346 A1 | 5/2007 | Peterson et al. | |
| 2007/0122016 A1 | 5/2007 | Brejl et al. | |
| 2007/0140536 A1 | 6/2007 | Sehnert | |
| 2007/0159962 A1 | 7/2007 | Mathavu et al. | |
| 2007/0165917 A1 | 7/2007 | Cao et al. | |
| 2007/0192138 A1 | 8/2007 | Saito et al. | |
| 2007/0237380 A1 | 10/2007 | Iwase et al. | |
| 2008/0016111 A1 | 1/2008 | Keen | |
| 2008/0021877 A1 | 1/2008 | Saito et al. | |
| 2008/0126982 A1 | 5/2008 | Sadikali et al. | |
| 2008/0136838 A1 | 6/2008 | Goede et al. | |
| 2008/0279439 A1 | 11/2008 | Minyard et al. | |
| 2008/0300484 A1 | 12/2008 | Wang et al. | |
| 2009/0005668 A1 | 1/2009 | West et al. | |
| 2009/0022375 A1 | 1/2009 | Fidrich | |
| 2009/0080719 A1 | 3/2009 | Watt | |
| 2009/0091566 A1 | 4/2009 | Turney et al. | |
| 2009/0132586 A1 | 5/2009 | Napora et al. | |
| 2009/0150481 A1 | 6/2009 | Garcia et al. | |
| 2009/0182577 A1 | 7/2009 | Squilla et al. | |
| 2009/0213034 A1 | 8/2009 | Wu et al. | |
| 2009/0248442 A1 | 10/2009 | Pacheco et al. | |
| 2009/0268986 A1 | 10/2009 | Holstein et al. | |
| 2009/0326373 A1 | 12/2009 | Boese et al. | |
| 2010/0086182 A1 | 4/2010 | Luo et al. | |
| 2010/0131887 A1 | 5/2010 | Salazar-Ferrer et al. | |
| 2010/0211409 A1 | 8/2010 | Kotula et al. | |
| 2010/0246981 A1 | 9/2010 | Hu et al. | |
| 2011/0293162 A1 | 12/2011 | Pajeau | |
| 2012/0070048 A1 | 3/2012 | Van Den Brink | |
| 2012/0130729 A1 | 5/2012 | Raizada et al. | |
| 2012/0136794 A1 | 5/2012 | Kushalnagar et al. | |
| 2012/0163684 A1 | 6/2012 | Natanzon et al. | |
| 2012/0284657 A1 | 11/2012 | Hafey et al. | |
| 2013/0070998 A1 | 3/2013 | Shibata | |

(56) References Cited

U.S. PATENT DOCUMENTS

| | | | |
|---|---|---|---|
| 2013/0076681 A1 | 3/2013 | Sirpal et al. |
| 2013/0297331 A1 | 11/2013 | Zuehlsdorff et al. |
| 2014/0022194 A1 | 1/2014 | Ito |
| 2014/0142983 A1 | 5/2014 | Backhaus et al. |
| 2015/0160848 A1 | 6/2015 | Gkanatsios et al. |
| 2016/0034110 A1 | 2/2016 | Edwards |
| 2016/0335395 A1 | 11/2016 | Wu et al. |
| 2017/0038951 A1 | 2/2017 | Reicher |
| 2017/0039321 A1 | 2/2017 | Reicher |
| 2017/0039322 A1 | 2/2017 | Reicher |
| 2017/0039350 A1 | 2/2017 | Reicher |
| 2017/0039705 A1 | 2/2017 | Fram |
| 2017/0046014 A1 | 2/2017 | Fram |
| 2017/0046483 A1 | 2/2017 | Reicher |
| 2017/0046485 A1 | 2/2017 | Reicher |
| 2017/0046495 A1 | 2/2017 | Fram |
| 2017/0046870 A1 | 2/2017 | Fram |
| 2017/0053404 A1 | 2/2017 | Reicher |
| 2017/0206324 A1 | 7/2017 | Reicher |
| 2017/0293720 A1 | 10/2017 | Reicher |
| 2017/0301090 A1 | 10/2017 | Fram |

OTHER PUBLICATIONS

U.S. Appl. No. 13/572,547, filed Aug. 10, 2012, Reicher.
U.S. Appl. No. 13/572,552, filed Aug. 10, 2012, Reicher.
U.S. Appl. No. 14/687,853, filed Apr. 15, 2015, Reicher.
Interview Summary dated Jan. 25, 2010, in U.S. Appl. No. 11/268,261.
Office Action dated Mar. 3, 2015 in U.S. Appl. No. 14/095,123.
Interview Summary dated May 1, 2015 in U.S. Appl. No. 14/095,123.
Office Action, dated Dec. 29, 2014 in U.S. Appl. No. 14/298,806.
Interview Summary, dated Mar. 2, 2015 in U.S. Appl. No. 14/298,806.
Interview Summary, dated Mar. 4, 2015 in U.S. Appl. No. 11/942,687.
Non-Final Office Action dated Apr. 1, 2015 in U.S. Appl. No. 14/043,165.
Office Action dated Mar. 17, 2015 in U.S. Appl. No. 13/768,765.
Notice of Allowance dated Jan. 14, 2015 in U.S. Appl. No. 14/179,328.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
AGFA HealthCare, color brochure "IMPAX 6: Digital Image and Information Management," © 2012 Agfa HealthCare N. V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N. V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
Aspyra's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F 11/2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, Exam-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Fujifilm Medical Systems, Synapse® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, Synapse® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, synapse® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.

(56) References Cited

OTHER PUBLICATIONS

Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 REV 4 BC/MP 3001/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2105.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516.
Tahmoush, D. and Samet, H., A New Database for Medical Images and Information, 2007, Medical Imaging 2007; PACS and Imaging Informatics, vol. 6516. pp. 1-9.
U.S. Appl. No. 12/437,522, filed May 7, 2009, Fram.
Final Office Action dated Jul. 23, 2015 in U.S. Appl. No. 14/095,123.
Final Office Action, dated Jun. 17, 2015 in U.S. Appl. No. 14/298,806.
Office Action dated Oct. 14, 2014 in U.S. Appl. No. 14/043,165.
Interview Summary dated Jun. 11, 2015 in U.S. Appl. No. 13/768,765.
Philips, IntelliSpace: Multi-modality tumor tracking application versus manual PACS methods, A time study for Response Evaluation Criteria in Solid Tumors (RECIST). 2012, Koninklijke Philips Electronics N. V., in four pages.
U.S. Appl. No. 14/792,201, filed Sep. 6, 2015, Reicher.
U.S. Appl. No. 15/254,627, Systems and Methods for Interleaving Series of Medical Images, filed Sep. 1, 2016.

(56) References Cited

OTHER PUBLICATIONS

U.S. Appl. No. 14/095,123, Systems and Methods for Retrieval of Medical Data, filed Dec. 3, 2013.
U.S. Appl. No. 15/292,006, Systems and Methods for Viewing Medical 3D Imaging Volumes, filed Oct. 12, 2016.
U.S. Appl. No. 15/346,530, Systems and Methods for Matching, Naming, and Displaying Medical Images, filed Nov. 8, 2016.
U.S. Appl. No. 14/298,806, Smart Placement Rules, filed Jun. 6, 2014.
U.S. Appl. No. 11/942,687, Smart Forms, filed Nov. 19, 2007.
U.S. Appl. No. 14/043,165, Automated Document Filings, filed Oct. 1, 2013.
U.S. Appl. No. 11/944,000, Exam Scheduling With Customer Configured Notifications, filed Nov. 21, 2007.
U.S. Appl. No. 15/292,014, System and Method of Providing Dynamic and Customizable Medical Examination for, filed Oct. 12, 2016.
U.S. Appl. No. 15/292,023, Selective Display of Medical Images, filed Oct. 12, 2016.
U.S. Appl. No. 15/469,342, Rules-Based Rendering of Medical Images, filed Mar. 24, 2017.
U.S. Appl. No. 15/469,281, Rules-Based Processing and Presentation of Medical Images, filed Mar. 24, 2017.
U.S. Appl. No. 15/469,296, Computer-Aided Analysis and Rendering of Medical Images, filed Mar. 24, 2017.
U.S. Appl. No. 14/792,210, Dynamic Montage Reconstruction, filed Jul. 6, 2015.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
U.S. Appl. No. 15/140,346, Database Systems and Interactive User Interfaces for Dynamic Interaction With, and Sorting of, Digital Medical Image Data, filed Apr. 27, 2016.
U.S. Appl. No. 15/140,363, Database Systems and Interactive User Interfaces for Dynamic Interation With, and Comparison of, Digital Medical Image Data, filed Apr. 27, 2016.
U.S. Appl. No. 15/140,351, Database Systems and Interactive User Interfaces for Dynamic Interaction With, and Review of, Digital Medical Image Data, filed Apr. 27, 2016.
U.S. Appl. No. 15/140,348, Database Systems and Interactive User Interfaces for Dynamic Interaction With, and Indications of, Digital Medical Image Data, filed Apr. 27, 2016.
Non-Final Office Action dated Jan. 20, 2016, in U.S. Appl. No. 14/502,055.
Interview Summary dated Apr. 14, 2016, in U.S. Appl. No. 14/502,055.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Office Action dated Dec. 12, 2016, in U.S. Appl. No. 15/254,627.
Interview Summary dated Aug. 27, 2015 in U.S. Appl. No. 14/095,123.
Office Action dated Feb. 23, 2016 in U.S. Appl. No. 14/095,123.
Final Office Action dated Jul. 20, 2016 in U.S. Appl. No. 14/095,123.
Corrected Notice of Allowance dated Jun. 27, 2016, in U.S. Appl. No. 14/502,055.
Office Action dated Mar. 10, 2016 in U.S. Appl. No. 14/081,225.
Notice of Allowance dated Sep. 2, 2016 in U.S. Appl. No. 14/081,225.
Corrected Notice of Allowance dated Oct. 21, 2016 in U.S. Appl. No. 14/081,225.
Non-Final Office Action dated Mar. 18, 2016 in U.S. Appl. No. 14/244,431.
Interview Summary dated Jun. 17, 2016 in U.S. Appl. No. 14/244,431.
Notice of Allowance dated Aug. 18, 2016 in U.S. Appl. No. 14/244,431.
Corrected Notice of Allowance dated Nov. 16, 2016 in U.S. Appl. No. 14/244,431.
Office Action, dated Feb. 16, 2016 in U.S. Appl. No. 14/298,806.
Final Office Action, dated Jul. 21, 2016 in U.S. Appl. No. 14/298,806.
Final Office Action, dated Jan. 5, 2015 in U.S. Appl. No. 11/942,687.
PTAB Examiner's Answer, dated Feb. 25, 2016 in U.S. Appl. No. 11/942,687.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Appeal Brief dated Jul. 15, 2016 in U.S. Appl. No. 14/043,165.
Examiner's Answer dated Nov. 14, 2016, in U.S. Appl. No. 14/043,165.
Board Decision dated Mar. 23, 2016 in U.S. Appl. No. 11/944,000.
Office Action, dated Jul. 15, 2016 in U.S. Appl. No. 11/944,000.
Notice of Allowance, dated Jan. 30, 2017, in U.S. Appl. No. 11/944,000.
Notice of Allowance dated Aug. 28, 2015 in U.S. Appl. No. 13/768,765.
Notice of Allowability dated Nov. 20, 2015 in U.S. Appl. No. 13/768,765.
Notice of Allowability dated Jul. 28, 2016 in U.S. Appl. No. 13/768,765.
Office Action dated Aug. 13, 2015 in U.S. Appl. No. 14/687,853.
Notice of Allowance dated Feb. 25, 2016 in U.S. Appl. No. 14/687,853.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Rosset et al.: "OsiriX: An Open-Source Software for Navigating in Multidimensional DICOM Images," Journal of digital Imaging, Sep. 2004, pp. 205-216.
Sandberg, et al., "Automatic detection and notification of "wrong paitent-wrong location" errors in the operating room," Surgical Innovation, vol. 12, No. 3, Sep. 2005, pp. 253-260.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
Final Office Action dated May 15, 2017 in U.S. Appl. No. 14/540,830.
Interview Summary dated Jul. 28, 2017 in U.S. Appl. No. 14/540,830.
Notice of Allowance (corrected) dated Jul. 13, 2017 in U.S. Appl. No. 15/254,627.
Office Action dated Jun. 27, 2017 in U.S. Appl. No. 15/469,342.
Office Action dated Jun. 26, 2017 in U.S. Appl. No. 15/469,281.
Office Action dated Jun. 27, 2017 in U.S. Appl. No. 15/469,296.
Interview Summary dated Mar. 24, 2017 in U.S. Appl. No. 14/540,830.
Notice of Allowance dated Apr. 3, 2017 in U.S. Appl. No. 15/254,627.
Notice of Allowance dated Mar. 30, 2017 in U.S. Appl. No. 14/095,123.

(56) References Cited

OTHER PUBLICATIONS

Notice of Allowance, dated Apr. 12, 2017 in U.S. Appl. No. 14/298,806.
Notice of Allowance, dated Apr. 11, 2017 in U.S. Appl. No. 15/292,023.
Interview Summary dated Oct. 13, 2017 in U.S. Appl. No. 15/469,342.
Interview Summary dated Oct. 13, 2017 in U.S. Appl. No. 15/469,281.
Interview Summary dated Oct. 13, 2017 in U.S. Appl. No. 15/469,296.

* cited by examiner

SYSTEMS AND METHODS FOR VIEWING MEDICAL IMAGES

CROSS-REFERENCE TO RELATED APPLICATIONS

This application is a continuation of U.S. patent application Ser. No. 13/477,853, filed on May 22, 2012 and entitled "SYSTEMS AND METHODS FOR VIEWING MEDICAL IMAGES," which is a continuation of U.S. patent application Ser. No. 13/228,349, filed on Sep. 8, 2011 and titled "SYSTEMS AND METHODS FOR VIEWING MEDICAL IMAGES," now U.S. Pat. No. 8,244,014, which is a continuation of U.S. patent application Ser. No. 12/702,976, filed on Feb. 9, 2010 and titled "SYSTEMS AND METHODS FOR VIEWING MEDICAL IMAGES," now U.S. Pat. No. 8,019,138, which is a continuation of U.S. patent application Ser. No. 11/179,384, filed on Jul. 11, 2005 and titled "SYSTEMS AND METHODS FOR VIEWING MEDICAL IMAGES," now U.S. Pat. No. 7,660,488, which claims priority under 35 U.S.C. §119(e) to U.S. Provisional Application Ser. No. 60/625,690, filed on Nov. 4, 2004, each of which is hereby expressly incorporated by reference in its entirety.

BACKGROUND OF THE INVENTION

Field of the Invention

This invention relates to management and viewing of medical images and, more particularly, to systems and methods of tracking which portions of medical images have been displayed using predetermined display parameters.

Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and manipulating these digital images.

SUMMARY OF THE INVENTION

A pixel is the smallest changeable element of a digital image, where an image comprises a plurality of pixels. For example, a mammographic image may include an array of 4,000 horizontal by 6,000 vertical pixels. For all medical images, particularly for certain modalities such as mammography, for example, it is important that every image pixel is displayed on a display device and viewed by a viewer or reader, such as a doctor, nurse, or other medical staff member. For example, in the field of mammography, diagnosis of a cancer may only be detectable in a small number of pixels. Accordingly, if this small number of pixels is not viewed by the viewer or reader, a misdiagnosis may be given to the patient. If a mammography image comprises 16 million pixels (e.g., an image resolution of 4,000×4,000), all of the 16 million pixels cannot be simultaneously displayed on a display device with a resolution of 2,048×1,536 (a 3.2 Megapixel display). Thus, only about ⅕ of the 16 million pixels of the mammography image may be displayed simultaneously at full resolution on such a display device. In other words, if one elects to display the image at full resolution, the entire 4,000×4,000 pixel image cannot be simultaneously displayed on a 2,048×1,536 or smaller matrix monitor. If one elects to display the complete area of the image, the only alternative is to display the entire image at a reduced resolution, discarding a fraction of the pixels.

Because an entire medical image cannot be concurrently viewed at full resolution on a typical display device, software applications currently allow viewing of portions of medical images at full resolution on the display device. In some embodiments, a user may be required to adjust the portion of the medical image that is displayed at full resolution on the display device in an attempt to view all of the image pixels. For example, the viewer may select up to hundreds of portions of the image for sequential viewing at full resolution before the entire image has been viewed at full resolution. As those of skill in the art will appreciate, manually tracking which portions of an image have been viewed at full resolution is cumbersome and may not allow the viewer to accurately determine when all relevant portions of the image have been viewed at full resolution. Currently, there are no systems or methods for automatically tracking the portions of a medical image that have been displayed at full resolution, or for indicating those images for which all pixels have been presented on a display device at full resolution. Accordingly, portions of medical images may not be viewed at full resolution and important indicia in the medical image may be overlooked. Thus, systems and methods for tracking portions of a medical image that have been viewed at full resolution are desired. Furthermore, systems and methods for allowing a viewer of the medical image to visually distinguish those portions that have not been viewed at full resolution are desired.

In one embodiment, the invention comprises a method of viewing medical images on a display device coupled to a computing system, wherein the display device is configured to concurrently display N pixels of an image to a user. In one embodiment, the method comprises (a) receiving an image at the computing system, wherein the image comprises M pixels, wherein M is greater than N; (b) displaying on the display device a portion of the image comprising N pixels, wherein the image portion is displayed at full resolution; (c) determining whether each of the M pixels of the image has been displayed on the display device, and (d) in response to determining that not all of the M pixels of the image have been displayed on the display device, returning to step (b).

In another embodiment, the invention comprises a method of viewing a mammographic image in a viewing pane depicted on a display device, wherein the viewing pane is configured to display a predetermined number of pixels. In one embodiment, the method comprises displaying the mammographic image at a reduced resolution in the viewing pane, displaying a portion of the mammographic image at full resolution in the viewing pane, and displaying the mammography image at the reduced resolution in the viewing pane, wherein a portion of the reduced resolution image that corresponds with the portion of the mammographic image that was displayed at full resolution is visually distinguishable from the remaining portion of the reduced resolution image.

In another embodiment, the invention comprises a computing system for viewing a mammographic image. In one embodiment, the system comprises a display device depicting a viewing pane, means for displaying a portion of the mammographic image at full resolution in the viewing pane, and means for displaying the entire mammographic image at the reduced resolution in the viewing pane, wherein the portion of the mammographic image displayed at full resolution is visually distinguishable from the other portions of the reduced resolution mammographic image.

In another embodiment, the invention comprises a computing system for viewing a medical image. In one embodiment, the system comprises a display device having a predetermined number of pixels, an input interface configured to receive the medical image, an application module comprising software for initiating display of the medical image on the display device, and a processing unit configured to execute the software, wherein, in a first mode, the software initiates display of the entire medical image at a reduced resolution on the display device, in a second mode, the software initiates display of a portion of the medical image at full resolution on the display device, and, in a third mode, the software initiates display of the entire medical image at the reduced resolution on the display device, wherein a portion of the reduced resolution medical image corresponding to the portion of the medical image displayed at full resolution is visually distinguishable from the remaining portions of the reduced resolution medical image.

In another embodiment, the invention comprises a method of viewing medical images. In one embodiment, the method comprises selectively viewing portions of a high resolution image and verifying that the entire high resolution image has been viewed.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
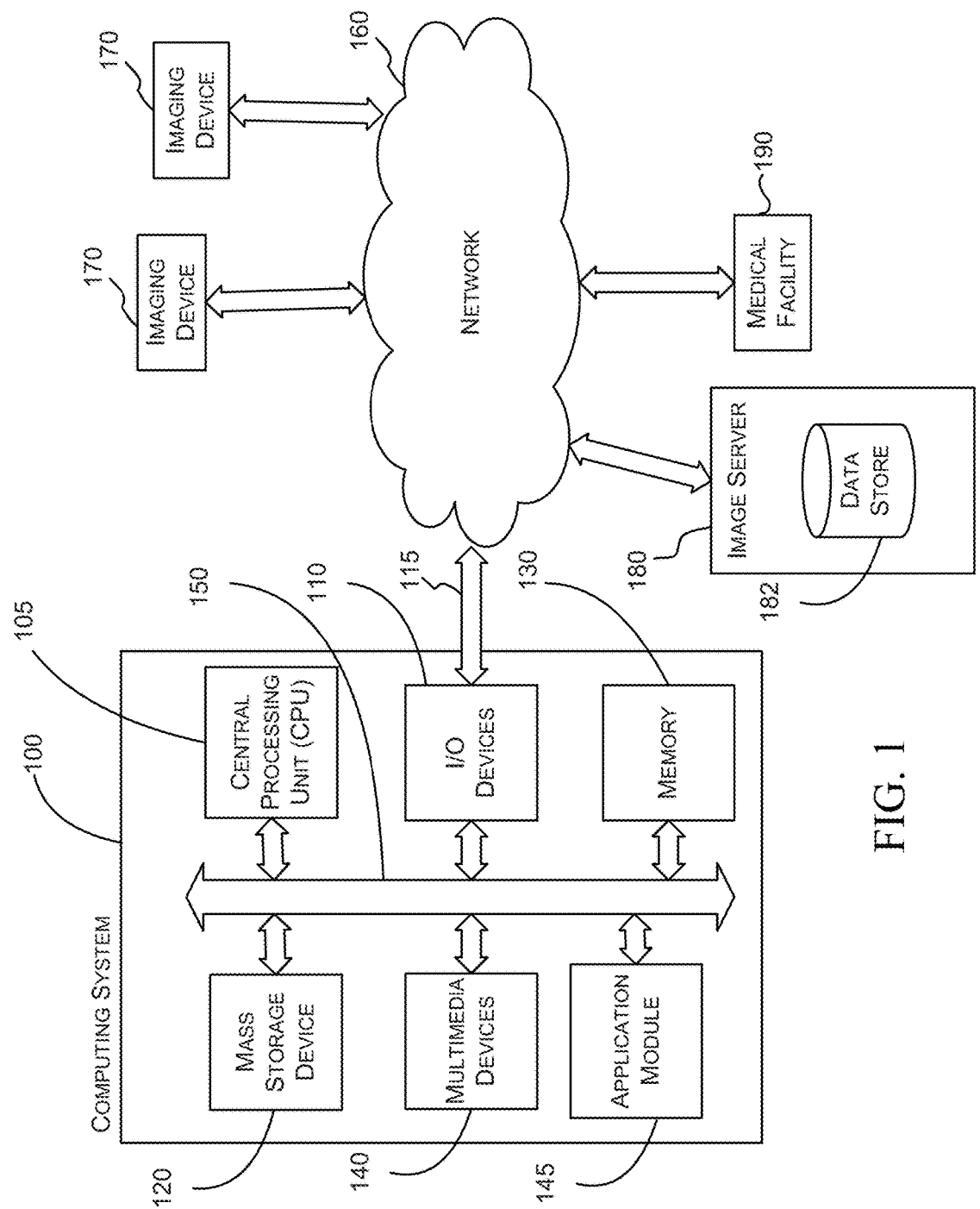
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server via the network 160 and image information is transmitted to the image server 160 and stored in the data store 182. In one embodiment, the image data is stored in Digital Imaging and Communications in Medicine ("DICOM") format. The complete DICOM specifications may be found on the National Electrical Manufactures Association Website at <medical.nema.org>. Also, *NEMA PS 3—Digital Imaging and Communications in Medicine,* 2004 ed., Global Engineering Documents, Englewood Colo., 2004, provides an overview of the DICOM standard. Each of the above-cited references is hereby incorporated by reference in their entireties. In one embodiment, the data store 182 also stores the user-defined display parameters associated with one or more of the images stored on the data store 182. As discussed in further detail below, the user-defined display parameters may vary depending of the type of image, area imaged, clinical indication, source of image, display device, user, or other factors. Accordingly, any type of user-defined display parameter is expressly contemplated for use in conjunction with the systems and methods described herein.

The exemplary image server 160 is configured to store images from multiple sources and in multiple formats. For example, the image server 160 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

Definition of Terms

Below is a definition of certain terms used herein.

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, and satellite images, for example.

"Modality" is defined as a medical imaging device (a patient who undergoes an MRI is said to have been examined with the MRI modality).

"Patient" refers to an individual who undergoes a medical imaging examination.

"Viewing" is defined to include the process of visually observing one or more medical images associated with exams.

"Viewer" is defined as any person who views a medical image.

"Reading" is defined to include the process of visually observing one or more medical images for the purpose of creating a professional medical report, also called an interpretation. When reading is complete, an exam may be labeled "read," indicating that the medical professional has completed observation of the one or more medical images for purposes of creating a medical report.

"Reader" is defined to include one who is authorized to perform the reading process.

"User" is defined to include any person that is a viewer and/or a reader.

"Display parameters" are defined to include methods of display of an image or exam. For example, an image or exam may be displayed with a certain pixel window level or width (similar to brightness and contrast), in color, based on a certain color map, opacity map, or other display parameters.

"Full pixel display" is defined to include display on a monitor or other display system of every pixel of a medical image.

"Full Resolution" is defined to include the concurrent display of all pixels of a medical image portion on a display device.

"Reduced Resolution" is defined to include display of less than all of the pixels of a medical image portion on a display device.

Figure 2:
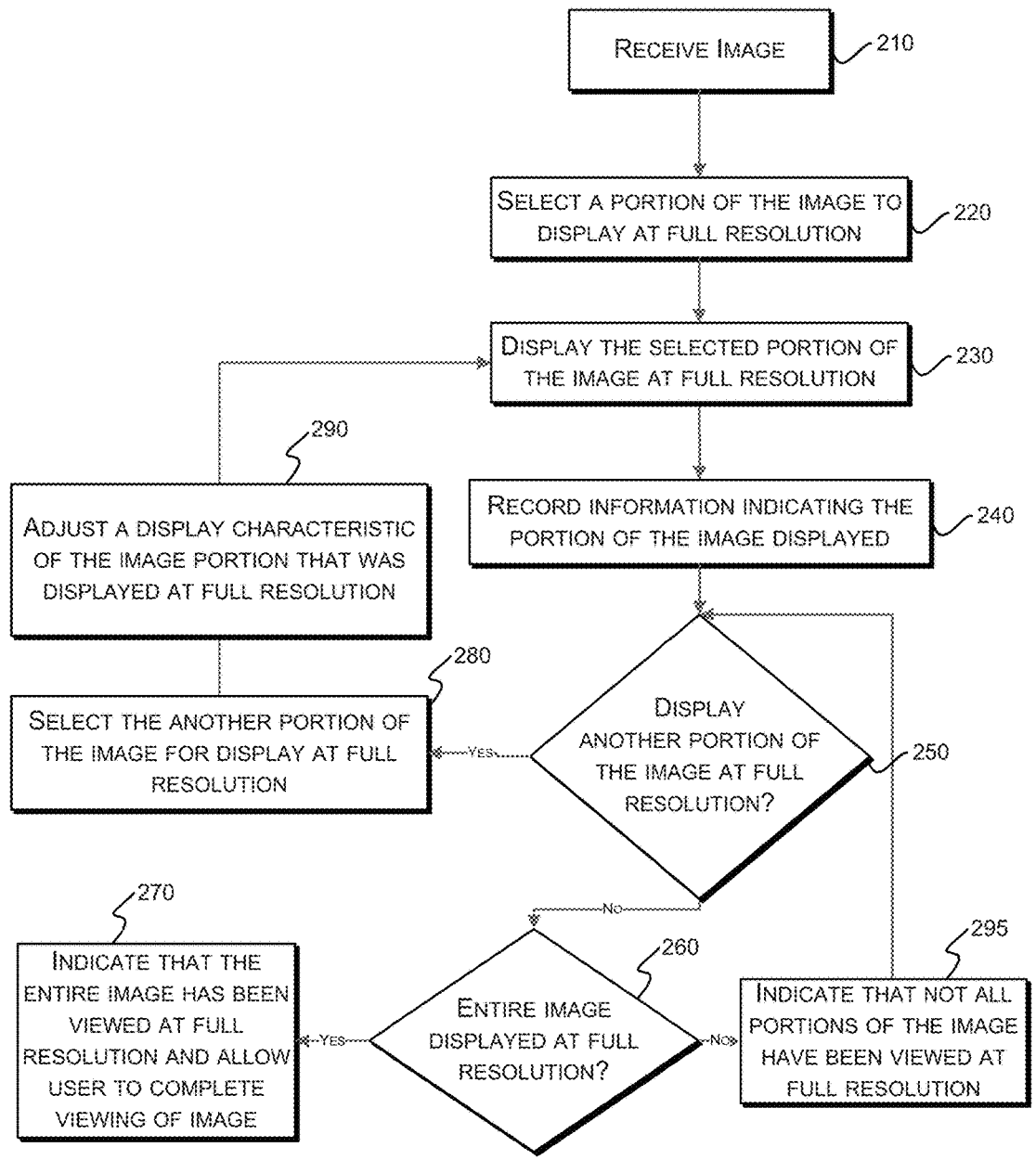
FIG. 2 is a flowchart illustrating a method of tracking which portions of a medical image have been displayed at full resolution.

"User-defined display parameter" refers to rules that a user can establish and store in a database that establish criteria for image display that is considered adequate. For example, a user-defined display parameter might store a rule that triggers certain warnings or displays if all pixels are not displayed or alternatively if at least half the pixels are not displayed, or alternatively, if some determined fraction of the pixels are not viewed with a certain display method (such as image window, level, brightness, contrast, opacity, color look-up table, or other parameters). User-defined display parameters may also refer to other image processing functions, such as edge enhancement and automated image analysis functions, e.g., computer-aided detection (CAD) techniques FIG. 2 is a flowchart illustrating a method of tracking which pixels of a medical image have been displayed according to user-defined display parameters. In one embodiment, the method described with respect to FIG. 2 is performed by a computing system 100, a medical facility 190, or an image server 190, for example. For ease of description, the method will be discussed below with reference to a computing system 100 performing the method. Depending on the embodiment, certain of the blocks described below may be removed, others may be added, and the sequence of the blocks may be altered.

In one embodiment, the user-defined display parameters specify that an entire medical image must be viewed at full resolution before a reader may mark the image as read. However, the user-defined display parameters may have different requirements, such as requiring that at least a defined portion of the pixels are displayed at full resolution and/or a defined portion of the pixels are viewed with a certain display method, for example. In another embodiment, the user-defined display parameters may specify that the medical image is viewed at a resolution that is less than full resolution. In other embodiments, the user-defined display parameters may specify additional display settings that must be satisfied in order to allow the reader to mark the image as read. For example, the display parameters may be set to require that every $n^{th}$ pixel is displayed. Thus, various user-defined display parameters may be established on a user, modality, or facility basis, for example. In one embodiment, such as when viewing CT images, the display parameters specify that the CT images must be viewed using a specified series of display parameters, such as lung windows, bone windows, and/or other types of windows, for example. In this embodiment, if the user forgets to view the images separately using all the required display parameters, the CT images may be misinterpreted. For ease of description, the following description refers to user-defined display parameters specifying that every pixel of the image is displayed at full resolution before it may be marked as read. However, the methods described herein are not limited to these display parameters and application of these methods using other user-defined display parameters are expressly contemplated. Any reference to tracking pixels at full resolution should be interpreted to cover similar systems and methods for monitoring and/or tracking of any other user-defined display parameter or combination of display parameters.

In some embodiments, it may be important and/or required that a user view all of a medical image at full resolution. Thus, a user may be required to adjust the portion of the medical image that is displayed at full resolution on the display device in an attempt to view all of the image pixels. However, currently there are no systems or methods for automatically tracking the portions of a medical image that have already been displayed at full resolution, or for indicating those images for which all pixels have been presented on a display device at full resolution ("full pixel display"). Accordingly, there is a need for image viewing devices and computing systems that monitor the portions of the medical image that are displayed on the display device, notate those portions that have been displayed at full resolution (or other user-defined display parameters), and provide the user with information indicating portions that have not been viewed at full resolution and/or provide information indicating for which images of a multiple image examination full pixel display has been accomplished. These processes are referred to herein as "visual pixel tracking."

In one embodiment, visual pixel tracking applies to the display of an individual image. In another embodiment, visual pixel tracking applies to a volume rendering, wherein after 3-D slicing, the computing system 100 indicates which pixels in a volume have not been displayed at full resolution or meeting other user-defined display parameters. FIG. 2, described in detail below, is a flowchart illustrating an exemplary method of tracking which pixels of a medical image are displayed according to user-defined display parameters. When volume rendering is performed, the method of FIG. 2 may be applied to each slice of the imaging volume. The user interface may provide a real time status of viewing each of the slices at full resolution.

In one embodiment, the computing system 100 is configured to determine a portion of the medical image on which visual pixel tracking is to be applied. Many medical images comprise areas surrounding the area of interest that are not important for a user, such as a doctor, to view and mark as read. For example, a medical image of a breast typically includes areas, such as air around the breast, that are irrelevant to the analysis by the user. Accordingly, viewing of these irrelevant portions of the image according to the user-defined display parameters is not necessary. In one embodiment, the computing system 100 analyzes the medical image and determines those areas that are irrelevant to the user's analysis. These irrelevant areas are then excluded from the user-defined display parameters and a viewer may mark an image as read without viewing the irrelevant areas at full resolution, for example. In another embodiment, the user may define the irrelevant areas of an image prior to viewing portions of the image at full resolution. For example, the user may use the keyboard, mouse, or other input device, to select areas surrounding the area of interest that do not require viewing according to the user-defined display parameters. In yet another embodiment, the user may determine that the relevant portions of an image have been viewed according to the display parameters, without the need to pre-select portions that should be viewed according to the display parameters. By providing for automatic and/or manual selection of irrelevant portions of a medical image, the viewer is not required to display those irrelevant portions of the medical image according to the user-defined display parameters, such as full resolution.

In a block 210, one or more medical images are received from an image source. Although the process described below is directed to processing one image, it is possible to use the process in conjunction with multiple images. The image source may comprise one or more of the imaging devices 170, the image server 180, the medical facility 190, or any other device that is capable of transmitting medical images. The medical image may be received via the network 160, or by other means, such as transferred on a floppy disk or CD-ROM. For ease of description, in the description that follows the exemplary computing system 100 will be the device that receives and displays the medical image. However, other computing devices may perform the methods described herein. The received medical image comprises more pixels that the display device and, thus, the entire image may not be concurrently displayed at full resolution.

Continuing to a block 220, a portion of the medical image is selected for display on the display device. As discussed above, many medical images contain more pixels than are capable of being displayed concurrently on a display device. Accordingly, the user of the medical image may select a portion of the image to display at full resolution on the display device. Alternatively, the computing system 100 may automatically determine a portion of the image to display on the display device. For example, in one embodiment the computing system 100 may initially display a top, left portion of received medical image first and then proceed to display adjacent portions of the image in response to an input from the user.

Moving to a block 230, the portion of the image that was selected for display at full resolution is displayed on the display device. More particularly, all of the image pixels for the selected portion of the medical image are concurrently displayed on the display device. In one embodiment, depending on the resolution of the medical image and the resolution of the display device, about 1-25% of the image may be concurrently displayed at full resolution on the display device.

Continuing to a block 240, an indication of the portion of the image that is displayed at full resolution is recorded. For example, if ⅛ of the total pixels of an image are displayed at full resolution, an indication of these pixels is recorded, such as by storing pixel information in a memory 130 of the computing system 100. Alternatively, the information regarding displayed pixels may be stored on a central server, such as the image server 180, which may then be accessible to other medical facilities and imaging devices.

In a decision block 250, the computing system 100 determines if another portion of the image has been selected for display at full resolution. In one embodiment, the user is presented with a reduced resolution representation of the medical image and is allowed to select another portion of the image for display at full resolution. Selection of an image portion may be accomplished by pressing certain keys on a keyboard, such as the arrow keys, for example. In another embodiment, the user may change the selected portion for viewing by moving a mouse, or other input device. For example, a pan tool may be invoked by the user, allowing the user to adjust the portion of the image displayed at full resolution so that areas of the images that are above, below, or to the sides of the current displayed portion are displayed at full resolution. In another embodiment, the computing system 100 may be configured to periodically updated the display with a portion of the image that has not yet been displayed at full resolution, or update the display in response to an input from the user.

If in the decision block 250, the computing device 100 determines that instructions have been received to display another portion of the image on the display device, at a block 280 the requested portion of the image is selected for display at full resolution. In one embodiment, such as when a panning tool is used, the selected portion comprises much of the currently displayed portion of the image. In another embodiment, the selected portion comprises a portion of the image that is entirely different than the portion of the image that is currently displayed.

Moving to a block 290, one or more display characteristics of the selected portion of the image that is displayed at full resolution is altered. Thus, when the entire image is displayed on the display device at a reduced resolution, those portions of the image that have not been displayed at full resolution can be identified. These portions of the image may then be selected for display at full resolution.

In one embodiment, the adjustment of a display characteristic comprises changing a color of the image portion. In another embodiment, other indicators, such as a line surrounding those image portions already displayed at full resolution, may be used to discriminate between portions of the image that have been displayed at full resolution and portions that have not been displayed at full resolution. Accordingly, when the entire image is viewed at a reduced resolution, such as by displaying only every $n^{th}$ image pixel, where n is less than or equal to the ratio of image pixels to display pixels, areas of the image that have not been viewed at full resolution are distinguished from those that have been viewed at full resolution. Based on the distinguishing display characteristic, the user may select for display a portion of the image that has not yet been displayed at full resolution. In one embodiment, coloring of the viewed pixels may be toggled on and off by the user. In another embodiment, a text message, icon, or other indication, may be displayed at the bottom of the display, for example, indicating that the image has been viewed according to the user-defined display parameters. In yet another embodiment, the outside margins of the viewing pane may change color or the system could beep or provide some other audible feedback when the image has been displayed according to the user-defined display parameters.

Moving from block 290, the selected portion of the image is displayed at full resolution in block 230, and the method continues to block 240 and block 250. Accordingly, blocks 230, 240, 250, 280, and 290 may be repeated multiple times in the process of selecting and displaying portions of an image at full resolution.

Referring again to the decision block 250, if the computing device 100 determines that instructions to display another portion of the image at full resolution have not been received, the method continues to a decision block 260, wherein the computing device 100 determines whether all of the image has been displayed at full resolution. If it is determined that not all of the image has been displayed at full resolution, the method continues to a block 295, wherein an indication is provided to the user that not all of the image has been viewed at full resolution. If, however, in the decision block 260, the computing device 100 determines that the entire image has been displayed at full resolution, the method continues to a block 270, wherein an indication is provided to the user that the entire image has been displayed at full resolution.

As noted above, the flowchart of FIG. 2 illustrates an exemplary process of tracking pixels viewed by a user according to exemplary user-defined display parameters. In particular, the user-defined display parameters in the example of FIG. 2 specify that the entire image is viewed at full resolution. However, in other embodiments the user-defined display parameters may require that, for example, only a portion of the image is displayed at full resolution, or any other predetermined reduced resolution. For example, many images contain non-rectangular areas of interest. The portions outside of the areas of interest, such as a breast in a mammography image, may include air, other body portions, or imaging equipment, for example. Those of skill in the art will recognize that is not important to analyze every pixel of the air surrounding an area or interest. Accordingly, in one embodiment, the user or the software may select portions of the image that must be displayed according to the user-defined display parameters. In another embodiment, the display parameters may specify that the viewer determines when the image has been viewed according to the user-defined display parameters. In this embodiment, the system may track the viewed pixel of the image, present the viewer with a view of the image that distinguishes portions of the image that have not been viewed at full resolution, or according to any other user-defined display parameters, and the viewer can determine whether the image can be marked as read.

In one embodiment, the user can establish user-defined display parameters and store those parameters in a database. For example, the user may establish a rule linked to the individual user, user type, exam type, modality, system or other links that triggers the above described automatic warnings and/or visual pixel tracking if a user-defined fraction of the pixels are displayed. The user may, alternatively or additionally, establish other rules linked to the individual user, user type, exam type, modality, and/or system that trigger the above-described automatic warnings and/or visual pixel tracking if an image is not viewed using one or more specified display parameters or combination of display parameters. For example, the computing system 100 may be configured to automatically direct the user to any pixels or images that have not been displayed with specific display parameters.

In another embodiment, rules may be generated to automatically designate when the pixel tracking process should be turned on and off. For example, rules may designate that visual pixel tracking applies to only certain viewers or users. In one embodiment, one type of display parameters can apply to one modality and another set of display parameters can apply to another modality.

In one embodiment, the user is not able to notate an image as being read, or completely viewed, until the entire image has been displayed at full resolution. Accordingly, in the exemplary method of FIG. 2, if not all of the image has been displayed at full resolution, the method indicates that the entire image has not been viewed at full resolution in block 295, and the method returns to block 250, wherein another portion of the image may be selected for viewing.

In one embodiment, the computing system 100 automatically displays portions of the image that have not yet been displayed at full resolution, and/or that have not been displayed such that user-defined display parameters have been met. For example, a user interface may include visual indications as to which portions of an image include pixels that have not been displayed, or which pixels have not been displayed using a user-defined display parameter, such as a specified window or level setting. In one embodiment, the computing system 100 automatically displays a message indicating which one or more of several images has not displayed with full pixel display and/or meeting user-defined display parameter criteria. In another embodiment, the computing system 100 automatically directs the user to any image positions or images, that have not been displayed at full resolution and/or meeting user-defined display parameter criteria.

Figure 3:
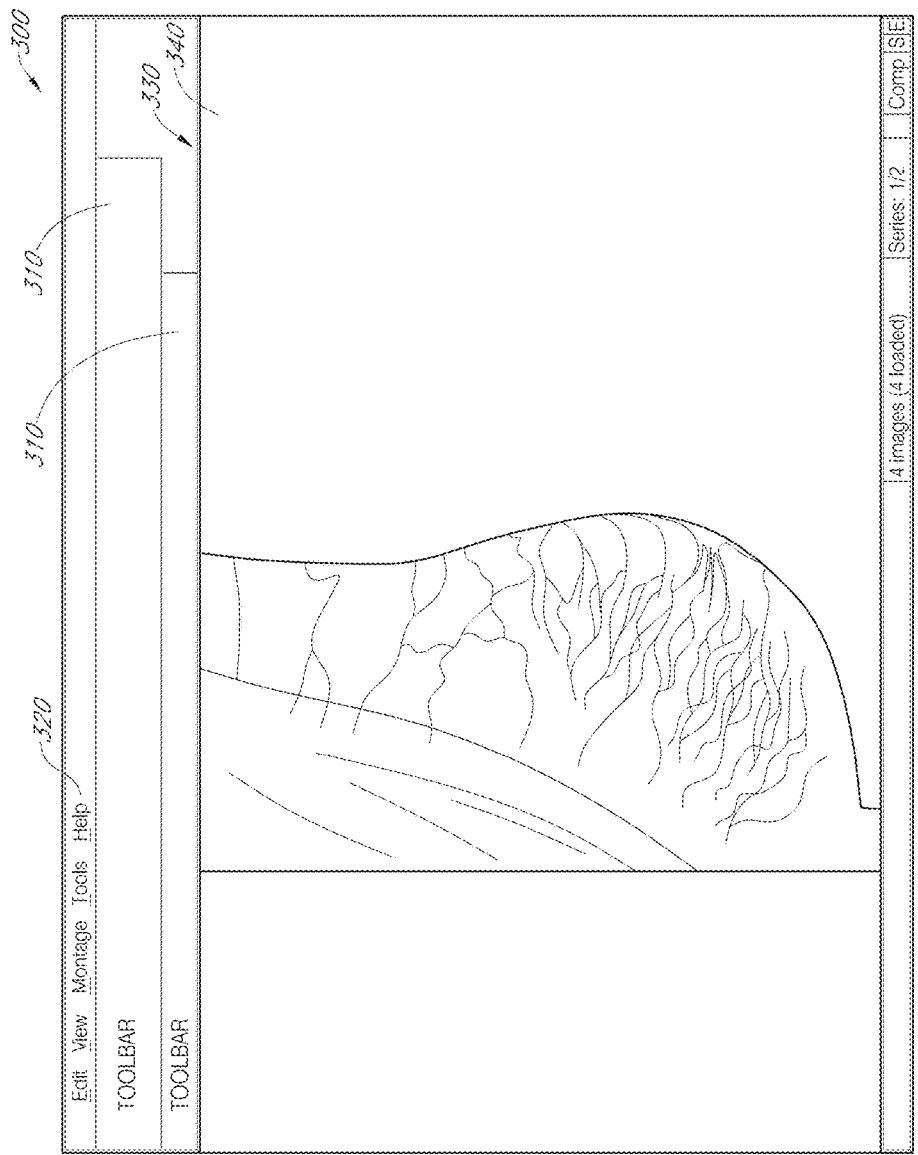
FIG. 3 is a mammographic image, wherein the entire medical image is displayed at a reduced resolution.

FIG. 3 is an exemplary graphical user interface (GUI) 300 including a menu bar 320, multiple toolbars 310, and an image viewing pane 330. In the example of FIG. 3, a mammographic image is displayed in the viewing pane 330, wherein the entire image is displayed at a reduced resolution. For example, if the mammography image comprises 16 million pixels (e.g., an image resolution of 4,000×4,000), all of the 16 million pixels cannot be simultaneously displayed on a display device with a resolution of 2,048×1,536 (a 3.2 Megapixel display). Thus, only about ⅕ of the 16 million pixels of the mammography image may be displayed simultaneously at full resolution on such a display device. Accordingly, in order to view the entire mammographic image on a display device, the number of pixels in the image is reduced by removing about 4 of every 5 pixels. Those of skill in the art will recognize that there are many systems and methods for reducing the resolution of a digital image. These systems and methods are contemplated for use in generating a reduced resolution image, such as the image displayed in the viewing pane 330 of FIG. 3.

As noted above, because many medical images, such as mammography images, for example, may include features or abnormalities that are only detectable by viewing only 1, or a few, pixels, a viewer of the image 340 may not be able to detect all features and abnormalities. Importantly, the viewer of a mammographic image displayed at less than full resolution, such as image 340, may not be able to detect an abnormality related to breast cancer. For example, the area 350 shown in FIG. 3 may include many times more pixel than are displayed in the area 350.

Figure 4:
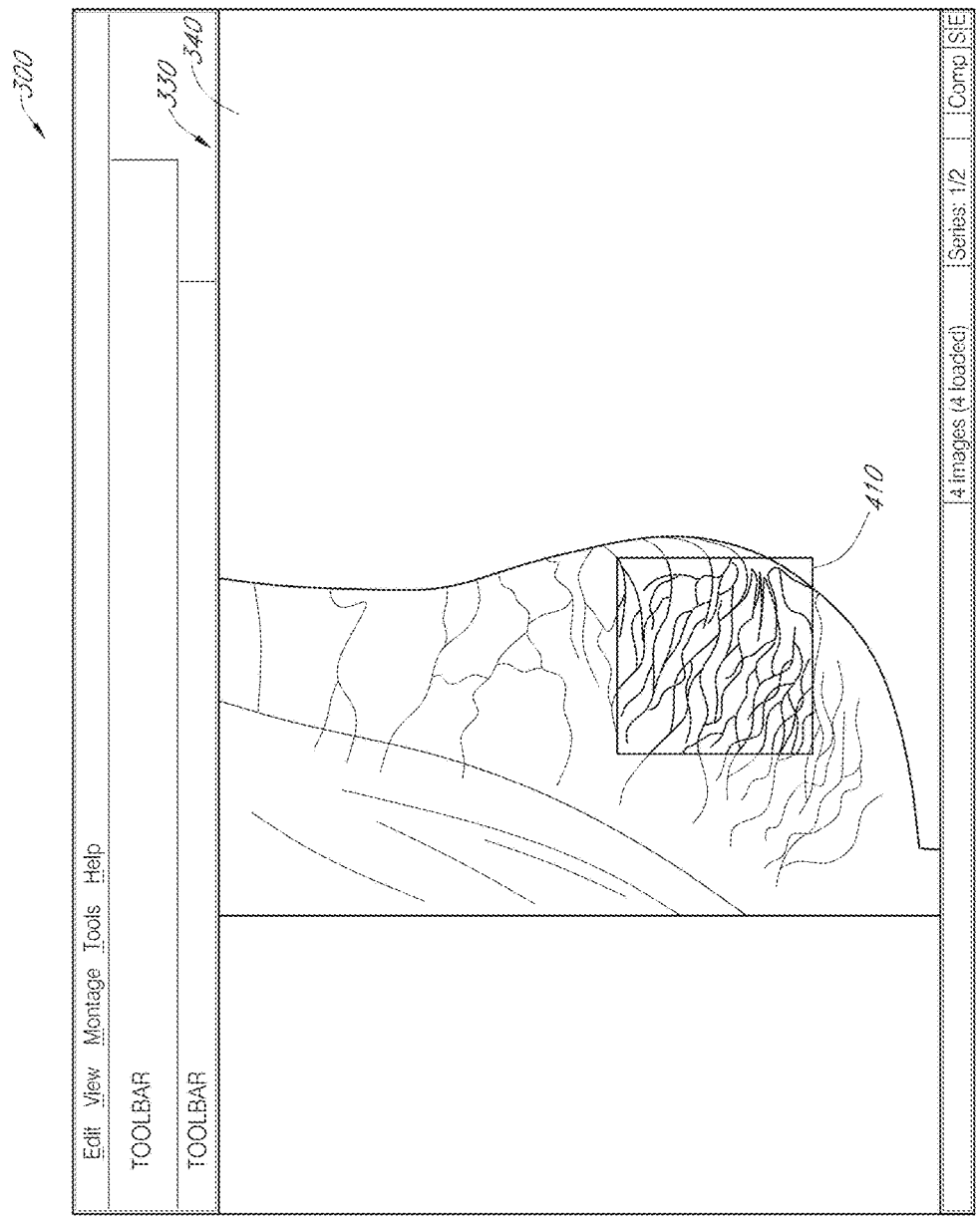
FIG. 4 is the mammographic image of FIG. 3, wherein a portion of the mammographic image is displayed at full resolution.
Figure 5:
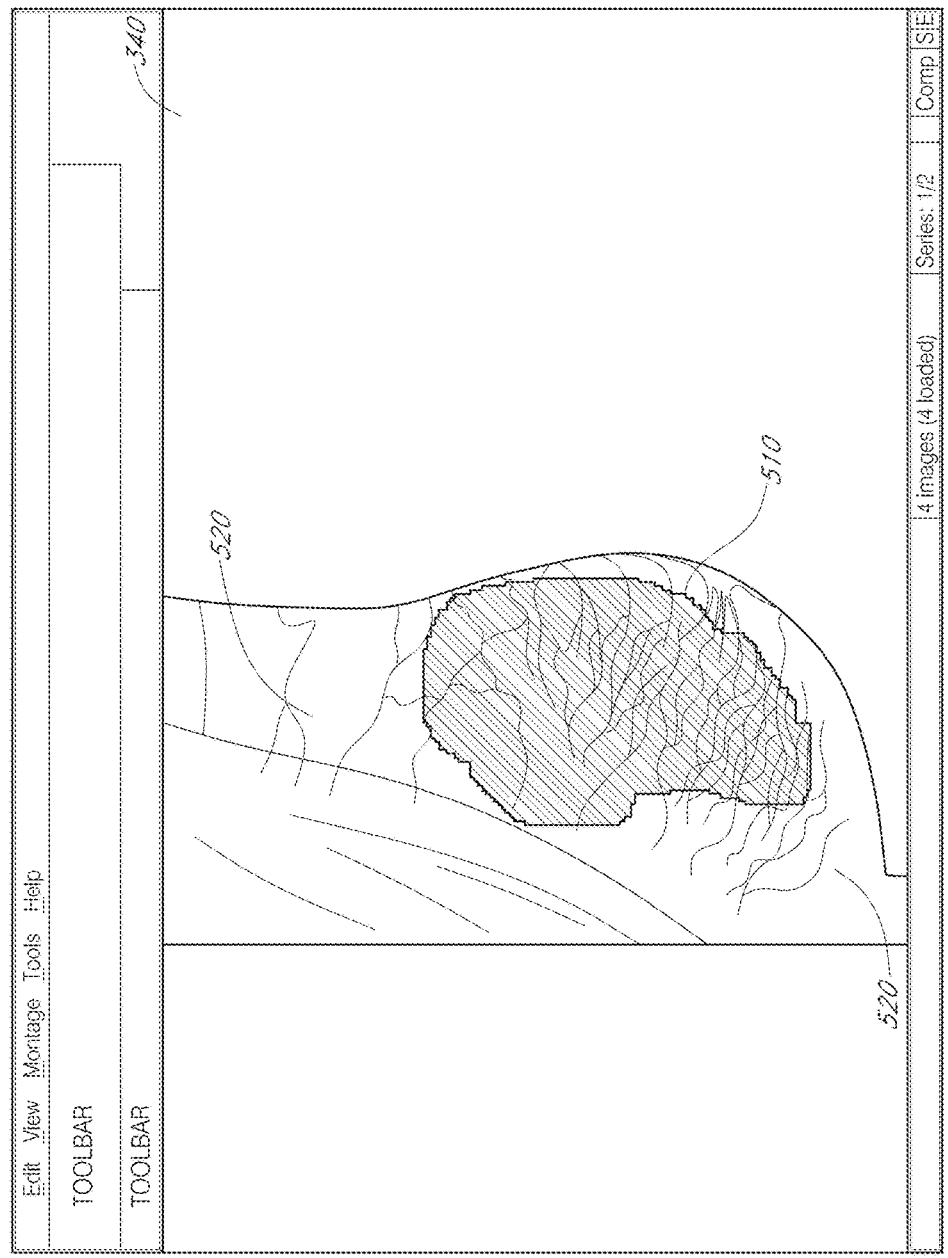
FIG. 5 is the mammographic image of FIG. 3, wherein portions of the image that have been displayed at full resolution are color inverted.

FIGS. 4 and 5 illustrate a method of sequentially viewing portions of a medical image at full resolution and related methods of tracking and indicating the portions of the image that have been viewed at full resolution. In the embodiment of FIGS. 4 and 5, the reduced resolution image remains in the viewing pane 330 while a portion of the image is also displayed at full resolution within the viewing pane 330.

FIG. 4 is the GUI 300 with the mammographic image 340 (FIG. 3) displayed in the viewing pane 330 at a reduced resolution, where a window 410 displays a portion of the image at full resolution. In one embodiment, the portion of the mammographic image that is displayed at full resolution in the window 410 is selected by the user, such as by allowing the user to move a cursor, or other icon, over portions of the mammographic image. In this embodiment, when the cursor is over an area of the mammographic image, the window 410 displays at full resolution the portion of the mammographic image currently covered by the cursor. Thus, in the example of FIG. 4, the window 410 display all of the pixels of a portion of the reduced resolution image 340.

In one embodiment, the portion of the image displayed at full resolution in the window 410 is updated as the user moves the cursor across the reduced resolution mammographic image 340. Thus, the user may determine the order in which portions of the reduced resolution image are viewed at full resolution and may control the speed at which portions of the image are viewed at full resolution.

FIG. 5 is the GUI 300 with the reduced resolution mammographic image 340 (FIG. 3) displayed in the viewing pane 330, wherein portions of the image that have been displayed at full resolution are distinguished from portions of the image that have not yet been displayed at full resolution. In the embodiment of FIG. 5, for example, the portions of the image that have already been viewed at full resolution, such as via the window 410 (FIG. 4) are color inverted from those portions that have not been viewed at full resolution. In FIG. 5, the non-inverted image portion 510 indicates that this portion has been displayed at full resolution. The inverted image portion 520, which substantially surrounds the non-inverted image portion 510, indicates that portion 520 has not been viewed at full resolution. Accordingly, if the viewer is required to view all of the image at full resolution, the portion 520 would need to be viewed at full resolution.

In another embodiment, the portions of the image that have been viewed at full resolution are distinguished from those portions that have not been viewed at full resolution in other manners. For example, in one embodiment a border may be displayed around those portions of the image 340 that have been displayed at full resolution. In another embodiment, the portion that has been viewed at full resolution is color-inverted. In another embodiment, the coloring of the portion that has been viewed at full resolution is adjusted, such as by adding a yellow tint to that portion.

Figure 6:
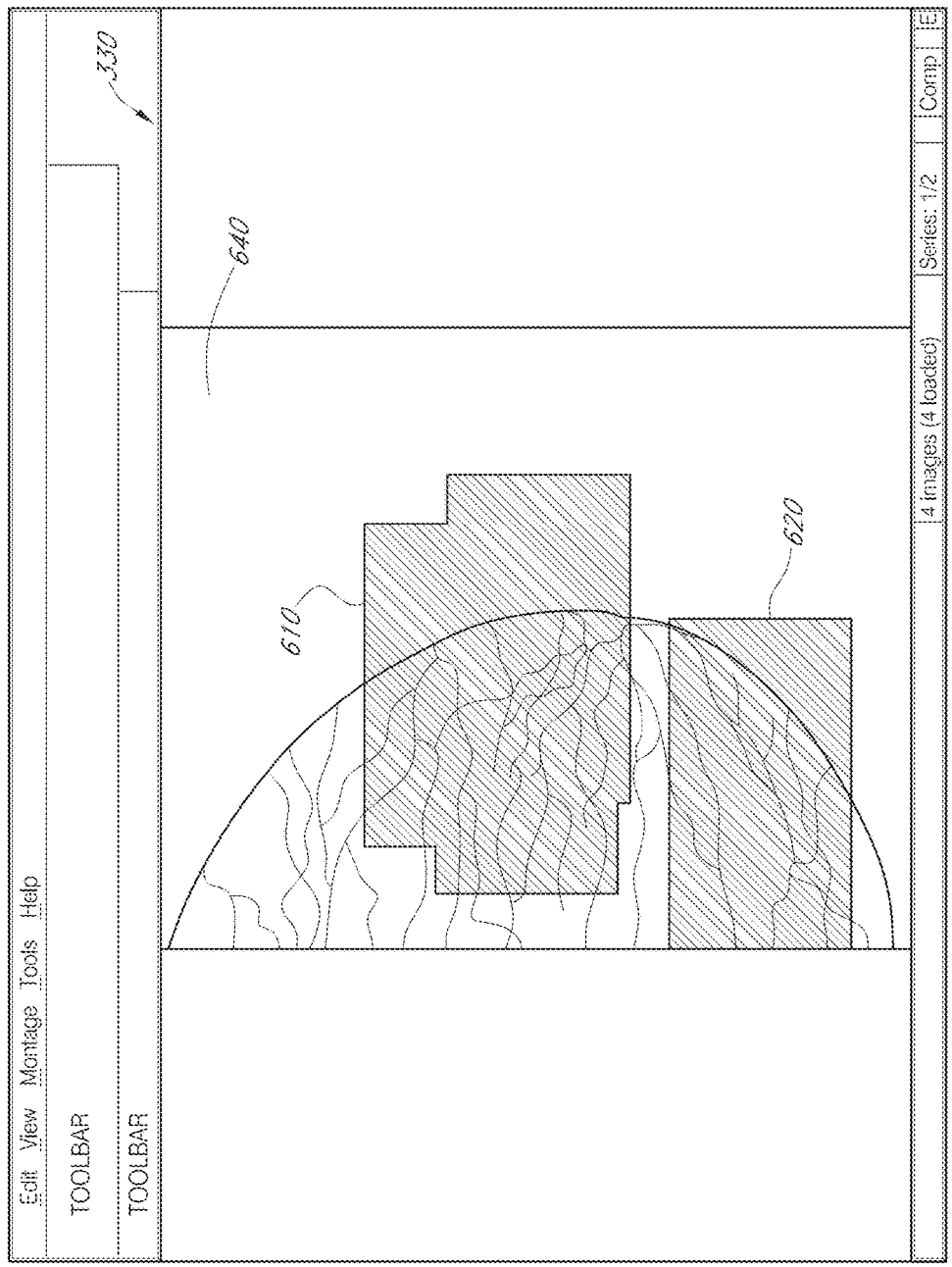
FIG. 6 is an exemplary mammographic image, wherein a portion of the image has been selected for display at full resolution and another portion of the image has already been displayed at full resolution.
Figure 7:
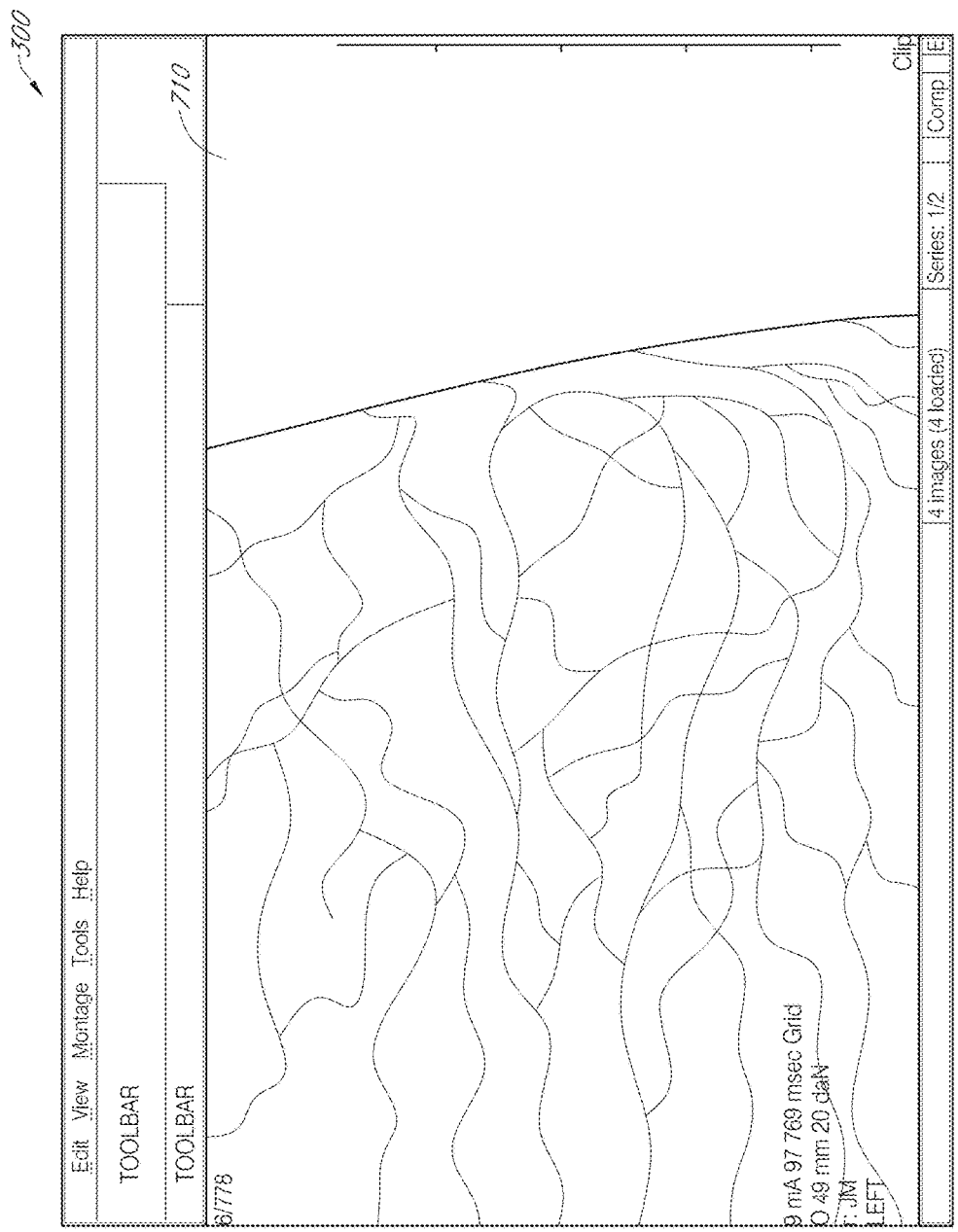
FIG. 7 is a portion of a mammographic image that has been selected for display at full resolution displayed at full resolution.

FIGS. 6 and 7 illustrate another method of sequentially viewing portions of a reduced resolution medical image at full resolution and related methods of tracking and indicating the portions of the image that have been viewed at full resolution.

FIG. 6 is the GUI 300 with the reduced resolution mammographic image 640 displayed in the viewing pane 330, wherein a portion of the image has already been displayed at full resolution and another portion of the image is selected for display at full resolution. More particularly, the inverted portion 610 of the image (shaped generally as two overlapping rectangles), indicates that portion 610 has already been displayed at full resolution. As described above, other methods of indicating portions of an image that have been viewed at full resolution may be used also.

In one embodiment, a portion of the mammographic image 640 is selected for display at full resolution. The portion that is selected is sized so that the selected portion may be displayed at full resolution in the viewing pane 330.

In FIG. 6, for example, the selection window 620 has approximately the same vertical to horizontal proportions as the viewing pane 330. In addition, the selection window 620 is sized so that a portion of the image covered by the selection window 620 substantially fills in the viewing pane 330 when displayed at full resolution.

In one embodiment, the viewer may move the selection window 620 to any portion of the viewing pane 330, such as by moving a mouse or pressing designated keys on a keyboard. Once the selection window 620 is over a portion of the image that the user would like to view at full resolution, the user selects the portion by pressing a button on the mouse or pressing a designated key on the keyboard, for example. In one embodiment, after selecting a portion for viewing at full resolution, the viewing pane 330 is updated to display the selected portion at full resolution in the viewing pane 330. After viewing the selected portion at full resolution for a predetermined period of time or until the user indicates, the viewing pane 330 is updated with the reduced resolution image 330, updated with an indication of the portion of the image that was viewed at full resolution. Alternatively, the viewing pane 330 may be sequentially filled with full resolution portions of the image without returning to the reduced resolution image.

FIG. 7 is the GUI 300 with a portion of a mammographic displayed at full resolution in the viewing pane 330. As noted above, many medical images, such as mammographic images, are taken at resolutions that are higher than resolutions of typical display and, thus, all pixel of these medical images may not concurrently be displayed. As illustrated in FIG. 7, a portion of a mammographic image is displayed at full resolution 710 in the viewing pane 330 of the GUI 300. The portion of the image displayed at full resolution in the viewing pane may be selected by the user (such as is described with reference to FIG. 6) or may be selected by the computing device according to predetermined display criteria.

In another embodiment, a viewing pane includes two panes, where a first pane, or selection pane, displays the image at a reduced resolution and a second pane, or display pane, displays at least a portion of the image at full resolution, or other user-defined display parameters. For example, a single display device could concurrently display an image such as the mammographic image 640 in the selection pane and a selected portion of the mammographic image 640 may be viewed in the display pane at full resolution, such as the full resolution image portion 710. In one embodiment, the selection pane may be sized to correspond to the size and shape that will accommodate a full resolution display pane. In one embodiment, the user may be provided with at least two methods of selecting portions of the reduced resolution image for viewing in the display pane. In particular, the user may move a selection window, such as the selection window 620 (FIG. 6), in the selection pane and the corresponding image area may be updated in the display pane. Alternatively, the user may use a pan function in the display pane and the position of the selection window in the selection pane is dynamically updated. In either case, areas that have been viewed at full resolution, or according to other user-defined display parameters, are dynamically adjusted so that they may be distinguished from the remaining portions. In an embodiment incorporating a selection and display pane, the relative sizes of the panes may be adjusted by the user or, alternatively, may be automatically adjusted by the software according to predetermined criteria.

In yet another embodiment, the selection pane may include multiple panes that each display a different image at a reduced resolution. For example, the multiple panes may display various images in a single image series. In one embodiment, the reduced resolution images are adjusted so that portions of the images that have been viewed at full resolution, or other user-defined display parameters, are visually distinguishable from the remaining portions. Accordingly, the display may provide an overview of the viewing status of multiple images.

The foregoing description details certain embodiments of the invention. It will be appreciated, however, that no matter how detailed the foregoing appears in text, the invention can be practiced in many ways. For example, the above-described pixel checking method may be performed on other types of images, in addition to medical images. For example, images of circuit boards, airplane wings, and satellite imagery may be analyzed using the described systems and methods for monitoring whether an image has been viewed according to predefined display parameters. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method for medical image display and analysis, the method comprising:
   by one or more processors executing program instructions,
       determining user-defined display parameters for display of an image on a display device, wherein the user-defined display parameters are associated with a user of the computing system, and wherein the image comprises a medical image;
       selectively displaying, in response to inputs by the user, regions of the image on the display device, wherein the regions of the image are displayed according to the user-defined display parameters and at a first resolution;
       storing tracking information indicating portions of the image that have been displayed on the display device according to the user-defined display parameters and at the first resolution;
       displaying a reduced resolution version of the image on the display device, wherein:
           the reduced resolution version of the image is displayed at a second resolution that is lower than the first resolution, and
           the reduced resolution version of the image includes visual indications, based on the tracking information, of the portions of the image that have been displayed on the display device according to the user-defined display parameters and at the first resolution; and
       in response to determining, based on at least the stored tracking information and the user-defined display parameters, that a relevant portion of the image has not been displayed, providing a visible and/or audible notification to a user.

2. The method of claim 1, wherein the visible and/or audible notification indicates that at least the relevant portion of the image has not been displayed according to the user-defined display parameters and at the first resolution.

3. The method of claim 2, wherein the visible and/or audible warning notification further indicates at least a second portion of the image that has been displayed according to the user-defined display parameters and at the first resolution.

4. The method of claim 1 further comprising:
receiving input from the user adding to and/or removing portions of the image determined to be relevant by the computing system.

5. The method of claim 1, wherein the user-defined display parameters are associated with an identity or role of a user.

6. The method of claim 1, wherein the user-defined display parameters indicate a percentage of pixels or portions of the image that must be displayed.

7. The method of claim 1, wherein the user-defined display parameters indicate one or more of an image window, a level, a brightness, a contrast, an opacity, or a color look-up table.

8. The method of claim 7, wherein the user-defined display parameters indicate more than one lung window or more than one bone window.

9. The method of claim 1, wherein the user-defined display parameters indicate one or more image processing functions.

10. The method of claim 9, wherein the one or more image processing functions include one or more of edge enhancement, automated image analysis, or computer-aided detection.

11. The method of claim 1, wherein the user-defined display parameters vary depending on one or more of a type of image, an area imaged, a clinical indication, a source of the image, a display device, and/or a user.

12. The method of claim 1, wherein the regions of the image and the reduced resolution version of the image are displayed on the display device simultaneously.

13. The method of claim 1, further comprising:
automatically analyzing, by the one or more processors, the image to determine portions of the image that are irrelevant for display according to the user-defined display parameters and at the first resolution.

14. A system configured for medical image display and analysis, the system comprising:
one or more hardware processors; and
a non-transitory computer readable medium operatively coupled to the one or more hardware processors and storing executable instructions configured for execution by the one or more processors in order to:
determine a characteristic associated with an image to display, wherein the image comprises a medical image;
determine required display parameters for display of the image, wherein the required display parameters are associated with the determined characteristic, and wherein the required display parameters indicate a first resolution at which the image is to be displayed;
store tracking information indicating portions of the image that have been displayed on a display device according to the required display parameters including at the first resolution;
causing display of a reduced resolution version of the image on the display device, wherein:
the reduced resolution version of the image is displayed at a second resolution that is lower than the first resolution, and
the reduced resolution version of the image includes visual indications, based on the tracking information, of the portions of the image that have been displayed on the display device according to the required display parameters including at the first resolution; and
in response to determining, based on at least the stored tracking information and the required display parameters, that a relevant portion of the image has not been displayed, provide a notification to a user of the system.

15. The system of claim 14, wherein the executable instructions are further configured for execution by the one or more processors in order to:
determine the relevant portion of the image.

16. The system of claim 15, wherein the relevant portion of the image includes all of the image.

17. The system of claim 15, wherein the relevant portion excludes areas of the image that represent air.

18. The system of claim 14, wherein the required display parameters further indicate more than one lung window or more than one bone window.

19. The system of claim 14, wherein the required display parameters further indicate one or more image processing functions.

20. The system of claim 19, wherein the one or more image processing functions include one or more of edge enhancement, automated image analysis, or computer-aided detection.

* * * * *